US009513555B2

(12) United States Patent
Shin et al.

(10) Patent No.: US 9,513,555 B2
(45) Date of Patent: Dec. 6, 2016

(54) METHOD FOR MANUFACTURING A SUSPENDED SINGLE CARBON NANOWIRE AND PILED NANO-ELECTRODE PAIRS

(71) Applicants: SK INNOVATION CO., LTD., Seoul (KR); UNIST ACADEMY-INDUSTRY RESEARCH CORPORATION, Ulsan (KR)

(72) Inventors: Heung-Joo Shin, Ulsan (KR); Jeong-Il Heo, Gyeonggi-do (KR); Yeong-Jin Lim, Busan (KR)

(73) Assignees: SK INNOVATION CO., LTD., Seoul (KR); UNIST ACADEMY-INDUSTRY RESEARCH CORPORATION, Ulsan (KR)

( * ) Notice: Subject to any disclaimer, the term of this patent is extended or adjusted under 35 U.S.C. 154(b) by 0 days.

(21) Appl. No.: 14/781,261

(22) PCT Filed: Mar. 28, 2014

(86) PCT No.: PCT/KR2014/002670
§ 371 (c)(1),
(2) Date: Sep. 29, 2015

(87) PCT Pub. No.: WO2014/157991
PCT Pub. Date: Oct. 2, 2014

(65) Prior Publication Data
US 2016/0054659 A1 Feb. 25, 2016

(30) Foreign Application Priority Data

Mar. 29, 2013 (KR) .................. 10-2013-0034415
Mar. 28, 2014 (KR) .................. 10-2014-0037107

(51) Int. Cl.
*G03F 7/40* (2006.01)
*G03F 7/16* (2006.01)
(Continued)

(52) U.S. Cl.
CPC ................ *G03F 7/40* (2013.01); *B82Y 40/00* (2013.01); *G01N 27/3278* (2013.01);
(Continued)

(58) Field of Classification Search
CPC .. G03F 7/0002; G03F 7/2002; G03F 7/2022; G03F 7/203; G03F 7/40; G03F 7/16; G03F 7/20; G01N 27/403; G01N 27/407; G01N 27/4075; G01N 27/30; G01N 33/0004; H01L 21/28; B82Y 40/00; B82Y 15/00; B82B 3/00
USPC ........ 430/198, 320, 329, 394, 330; 977/762, 977/900, 901
See application file for complete search history.

(56) References Cited

U.S. PATENT DOCUMENTS

| 2010/0051446 | A1 | 3/2010 | Wang et al. | |
|---|---|---|---|---|
| 2014/0079921 | A1* | 3/2014 | De Volder | B82Y 30/00 428/196 |
| 2014/0353152 | A1* | 12/2014 | Shin | G01N 27/3278 204/403.01 |

FOREIGN PATENT DOCUMENTS

WO    WO 2009/069846 A1 *  6/2009

OTHER PUBLICATIONS

Lim et al., "Monolithic Carbon Structures Including Suspended Single Nanowires and Nanomeshes as a Sensor Platform", Nanoscale Research Letters, vol. 8, No. 1, pp. 1-9 (Nov. 2013).*
Sharma, S., et al., Increased graphitization in electrospun single suspended carbon nanowires integrated with carbon-MEMS and carbon-NEMS platforms, ACS applied materials & interfaces, Jan. 3, 2012, pp. 34-39, vol, 4, No. 1.

(Continued)

*Primary Examiner* — John A McPherson
(74) *Attorney, Agent, or Firm* — IP & T Group LLP

(57) ABSTRACT

The present invention provides a method for manufacturing a suspended single carbon nanowire and piled nano-electrode pairs, and a suspended single carbon nanowire and piled nano-electrode pairs manufactured using said method. A suspended single carbon nanowire, which is manufactured at a high yield by the method for manufacturing a suspended single carbon nanowire according to the present invention, has a minimized dimension, and a suspended carbon nanomesh, which is manufactured at a high yield by the method for manufacturing piled nano-electrode pairs according to the present invention, is thin and dense. The present invention also provides a gas sensor or an electrochemical sensor, to which a suspended single carbon nanowire and piled nano-electrode pairs manufactured by the method according to the present invention are applied.

15 Claims, 9 Drawing Sheets

(51) Int. Cl.
- *G03F 7/20* (2006.01)
- *G03F 7/32* (2006.01)
- *G01N 33/00* (2006.01)
- *B82Y 40/00* (2011.01)
- *G01N 27/327* (2006.01)
- *B82Y 15/00* (2011.01)

(52) U.S. Cl.
CPC ........... *G01N 33/0004* (2013.01); *G03F 7/16* (2013.01); *G03F 7/20* (2013.01); *G03F 7/32* (2013.01); *B82Y 15/00* (2013.01)

(56) References Cited

OTHER PUBLICATIONS

Heo, J., at al., Scalable suspended carbon nanowire meshes as ultrasensitive electrochemical sensing platforms, 2012 IEEE 25th International Conference on Micro Electro Mechanical Systems (MEMS), 2012, pp, 878-881. (Jan. 2012).

Penmatsa, V., et al., Fabrication of carbon nanostructures using photo-nanoimprint lithography and pyrolysis, Journal of Micromechanics and Microengineering, 2012, p. 045024, vol. 22, No. 4. (Mar. 2012).

* cited by examiner

METHOD FOR MANUFACTURING A SUSPENDED SINGLE CARBON NANOWIRE AND PILED NANO-ELECTRODE PAIRS

This application is a national stage application of PCT/KR2014/002670 filed on Mar. 28, 2014, which claims priority of Korean patent applications number 10-2013-0034415 and 10-2014-0037107, filed on Mar. 29, 2013 and Mar. 28, 2014, respectively. The disclosure of each of the foregoing applications is incorporated herein by reference in its entirety.

TECHNICAL FIELD

The present invention relates to a method for manufacturing a suspended single carbon nanowire and piled nano-electrode pairs, and a suspended single carbon nanowire and piled nano-electrode pairs manufactured by the methods. More specifically, the present invention relates to a method for manufacturing a suspended single carbon nanowire for minimizing a dimension of the suspended single carbon nanowire, and a method for manufacturing piled nano-electrode pairs for forming thin and dense suspended carbon nanomeshes. The present invention relates to a gas sensor or an electrochemical sensor to which the suspended single carbon nanowire and the piled nano-electrode pairs manufactured by the methods of the present invention are applied.

BACKGROUND ART

In accordance with increase of interest in environmental issues and development of info-communication equipment, sensors for various gases have been developed. By grafting the sensors with semiconductor technology, it is easy to manufacture the sensors, and the manufactured sensors have improved performance. A primary goal of all sensors is to increase sensitivity for improving performance, and an effort to achieve this goal has also been increased.

Meanwhile, since a semiconductor gas sensor in the related art includes a semiconductor thin film as a sensing material, there is limitation in sensitivity. For example, it is almost impossible to sense stable chemical materials such as carbon dioxide ($CO_2$).

Accordingly, in the sensor for sensing harmful gases such as carbon monoxide (CO), carbon dioxide, and the like, an electrochemical method using electrolyte solution, an optical method using infrared absorption, and a method for measuring electrical resistance of nano particles or nanowire have been applied.

The electrochemical method is to measure current flowing in external circuits caused by electrochemically oxidizing or reducing target gas, or to use electromotive force generated from ions in gas phase dissolved or ionized in an electrolyte solution or a solid, acting on an ionic electrode, which has disadvantages in that a reaction rate is extremely low, gas sensing range and environment for using the sensor are limited, and the cost is also high.

In addition, the optical method using infrared absorption is advantageous in sensing because it is rarely affected by other mixed gases or humidity; however, it has disadvantages such as complicated device, large dimension, and high cost.

Structures of chemical sensors are generally based on catalytic combustion type sensors, such that when the gas reacts with a platinum wire integrated in the sensor as a catalyst, the sensor is capable of sensing the gas by measuring change in resistance of the platinum wire resulted by endothermic reaction or exothermic reaction at the platinum wire, to thereby have improved stability and sensitivity of the sensor.

Meanwhile, as the relationship between contact reaction by chemical adsorption of a gas and electron density has been identified and an oxide semiconductor-type gas sensor has been developed and commercialized, the semiconductor-type gas sensor has been developed to be capable of sensing most gases including a combustible gas, which achieves miniaturization, cost reduction and improvement in reliability as compared to gas sensors based on other schemes.

As compared to other sensors that are required to be heated up to about 300° C. to detect nitrogen oxide, and the like, a gas sensor using carbon nanotube as one of the semiconductor-type gas sensor has advantages in that its sensitivity is thousands of times higher than those of other sensors because of its nanoscale size and it is able to be operated even at room temperature.

Gas sensors of measuring change in electrical resistance of a nanomaterial itself or a material coated on the nanomaterial according to concentration of a gas to be measured, has been developed. When the nanomaterials are used, the surface to volume ratio is significantly high, such that the effect of the surface reaction corresponding to the gas concentration change on the electrical resistance change in the volume is significantly large, thereby making it possible to manufacture a sensor having significantly high sensitivity.

Generally, in the existing sensors using nanoparticles or nanowires, electrical resistance is measured by connecting electrodes capable of measuring change in electrical resistance of nanomaterials only at specific portions of the nanomaterials dispersed non-uniformly on the substrate, or positioning the nanomaterials on the pre-patterned electrodes by flowing the nanomaterials or electrospinning the nanomaterials. These methods have disadvantages in that physical and electrical connections between the nanomaterials and the electrodes are unstable, and the nanomaterials being in contact with the substrate are affected by the substrate in a gas sensing process.

Afterward, a suspended nanowire-based sensor disclosed in Non-Patent Document 1 is manufactured by adhering a nanowire onto electrodes spaced apart from the surface at a predetermined gap, that is, attaching nanowires onto post-shaped electrodes using electrospinning, or selectively growing the nanowires from one electrode to another electrode in the opposite side. The existing suspended nanowire-based sensors have insufficient sensitivity, poor contact between the nanowire and the electrodes, difficulty in controlling manufacturing processes due to complexity of the processes, which causes reduction in yield, and require high fabrication cost and long process time. Therefore, the sensor has limitation in commercialization through mass-production of the sensor.

NON-PATENT DOCUMENT (Non-Patent Document 1) S. Sharma, A. Sharma, Y.-K. Cho, M. Madou, Applied Materials and Interface 2012, 4, 34-39.

DISCLOSURE

Technical Problem

An object of the present invention is to provide a method for manufacturing a suspended single carbon nanowire capable of effectively overcoming limitations of the existing suspended nanowire sensor such as reduction in yield, limitations in fabrication, and the like, and a method for manufacturing piled nano-electrode pairs which is an example to which the method for manufacturing the suspended single carbon nanowire is applied.

Another object of the present invention is to provide a method for manufacturing a suspended single carbon nanowire for minimizing the dimension of the suspended single carbon nanowire, and a method for manufacturing piled nano-electrode pairs for forming thin and dense suspended carbon nanomeshes, in order to effectively overcoming limitations of the existing suspended nanowire.

Another objective of the present invention is to provide a gas sensor or an electrochemical sensor to which the suspended single carbon nanowire and the piled nano-electrode pairs manufactured by the methods of the present invention are applied.

Technical Solution

In one general aspect, a method for manufacturing a suspended single carbon nanowire includes:
(a) depositing an insulation layer 11 on a substrate 10;
(b) coating a photoresist 12 on the insulation layer;
(c) forming photoresist post parts 13 on an upper portion of the insulation layer by primarily exposing the photoresist through a photomask having a post shape;
(d) forming a micro-photoresist wire 14 connecting the photoresist post parts to each other by secondarily exposing an upper portion of the photoresist between the photoresist post parts in a shape of a micro-sized wire connecting the photoresist post parts through a photomask having a wire shape;
(e) removing the photoresist of a remaining portion except for portions exposed in steps (c) and (d) by performing a development process; and
(f) forming the suspended single carbon nanowire 16 by pyrolyzing the photoresist post parts 13 and the micro-sized wire 14 remaining after step (e),
wherein the pyrolysis of step (f) is performed in two steps including a first step and a second step, and the second step is performed at a temperature higher than that of the first step (FIG. 1).

A type of the substrate 10 is not specifically limited so as to achieve the object of the present invention. Preferably, the substrate may be a silicon substrate, and more preferably, a silicon wafer. Here, when the silicon wafer is used as the substrate, the substrate may have a general size within 6 to 9 inches.

The insulation layer 11 deposited on the substrate in step (a) above may be made of any materials capable of preventing electrical connection between two carbon posts 15, for example, silicon dioxide or silicon nitride. In addition, in step (a) above, the insulation layer may be preferably deposited on the entire upper surface of the substrate. Here, the deposition may be performed by non-limiting methods known to a person skilled in the art, for example, deposition by thermal oxidation.

When the substrate is an insulator in step (a) above, a step of depositing the insulation layer may be omitted. Examples of materials of the insulator substrate may include quartz, aluminum oxide, and the like.

After the insulation layer is deposited on the substrate in step (a), it is preferable to wash the deposited insulation layer through washing processes, before performing step (b) above. Here, specific methods of the washing processes are not limited, for example, washing with a piranha solution (a solution containing sulfuric acid ($H_2SO_4$) and hydrogen peroxide ($H_2O_2$) mixed at a ratio of 4:1) may be performed.

In step (b) above, the photoresist 12 may be uniformly coated on the insulation layer deposited on the substrate, wherein the coating may be performed by non-limiting methods known to a person skilled in the art. For example, the coating may be performed by various methods such as spin coating, dip coating, gravure coating, and the like. The photoresist coated in step (b) above is not limited in principle as long as the photoresist achieves the objects of the present invention, but preferably, the photoresist is a negative photoresist including SU-8 photoresist. Here, the photoresist to be coated may have a thickness of 5 μm to 75 μm, preferably, 20 μm to 40 μm.

After the photoresist is coated in step (b) above, it is preferable to perform a soft bake process on the insulation layer and the substrate on which the photoresist is coated, before performing step (c). Here, once the soft bake is completed, step (c) which is a next step may be performed after sufficiently cooling the substrate naturally and confirming that the temperature of the substrate after being cooled is the same as that of the substrate before step (a) above. Here, specific conditions of the soft bake correspond to 80° C. to 120° C. for 1 min to 15 min.

In step (c) above, the primary exposure may be performed by exposing the coated photoresist to ultraviolet rays through a photomask having a post shape by using a mask aligner. When the primary exposure is completed as described above, the photoresist is cured into a post shape on the upper portion of the insulation layer forming photoresist post parts 13. Here, the exposed light energy needs to be sufficient so that the photoresist is capable of being cured from the uppermost part of the photoresist down to just above the insulation layer.

After the primary exposure is performed in step (c) above, it is preferable to perform a post exposure bake on the insulation layer and the substrate in a state in which the photoresist post parts 13 are formed, before performing step (d). Here, once the post exposure bake is completed, it is required to sufficiently cool the substrate naturally, and confirm that the temperature of the substrate after being cooled is the same as that of the substrate before step (a) above. Here, specific conditions of the post exposure bake correspond to 80° C. to 120° C. for 1 min to 15 min.

In step (d), the secondary exposure may be performed by exposing an upper portion of the photoresist between the photoresist post parts 13 to ultraviolet rays, through a photomask having a shape of micro-sized wire. In the secondary exposure, only the upper end of the photoresist may be cured by limiting the energy of ultraviolet rays absorbed in the photoresist less than that of the primary exposure. Through the secondary exposure, a portion of the photoresist between the photoresist post parts may be cured to have a wire shape, thereby forming a micro photoresist wire 14 connecting the photoresist post parts to each other. Here, the micro photoresist wire is formed so as to be separated from the insulation layer at a predetermined distance.

After the secondary exposure of step (d) is performed, it is preferable to perform a post exposure bake on the insulation layer and the substrate in a state in which the photoresist post parts 13 and the micro photoresist wire 14 are formed, before performing step (e) above. Here, once the post exposure bake is completed, it is required to sufficiently cool the substrate naturally and to confirm that a temperature of the substrate after being cooled is the same as that of the substrate before step (a) above. The reason is that if the substrate is not sufficiently cooled, cracks or damage may occur on the photoresist post parts 13 and the micro photoresist wire 14 because of thermal stress in the development process of step (e). Here, specific conditions of the post exposure bake correspond to 80° C. to 120° C. for 1 min to 15 min.

In step (e) above, the photoresist of a remaining portion except for portions exposed in steps (c) and (d) is removed by performing a development process. The photoresist post parts 13 and the micro photoresist wire 14 in the suspended state only remain after the development process of the photoresist. In the development process, various kinds of developers known to a person skilled in the art, for example, an SU-8 developer, may be used.

After the development process of step (e) is performed, it is preferable to wash the portion remaining after the development process, before performing step (f). Specific methods for the washing are not limited, for example, the washing may be performed in a sequential order of isopropyl alcohol and methanol.

In addition, small residual particles which are not removed even though the development process of step (e) is performed, may exist. Accordingly, after the development process of step (e) is performed, it is preferable to clearly remove remaining small particles which are not removed in step (e), by using a photoresist asher, before performing step (f).

In step (f) above, the micro photoresist wire 14 and the photoresist post parts 13 remaining after step (e) may be pyrolyzed to form a suspended single carbon nanowire 16. Here, the photoresist post parts are converted into carbon posts 15 by pyrolysis, and the carbon posts 15 allow the suspended single carbon nanowire 16 formed by the pyrolysis to be separated from the insulation layer at a predetermined distance. A glass transition temperature of the micro photoresist wire 14 is approximately 250° C. However, as the pyrolysis proceeds, the glass transition temperature is increased while organic gas is discharged from the photoresist structures to the outside, and thus there does not occur significant overall shape change between the micro photoresist wire 14 before the pyrolysis and the carbon nanowire 16 formed after the pyrolysis (FIG. 2). In the pyrolysis, the micro photoresist wire 14 is converted into the carbon nanowire 16 without deflection. In addition, due to volume reduction of the post parts supporting the micro photoresist wire 14 in the pyrolysis, tensile stress is developed from the both edge of the carbon wire that is formed by the pyrolysis, and accordingly, the completed suspended carbon nanowire 16 maintains a straight shape.

Meanwhile, one object of the present invention is to provide the method for manufacturing a suspended single carbon nanowire for minimizing the dimension of the suspended single carbon nanowire, and accordingly, the present inventors found that specific conditions for the pyrolysis of step (f) is more preferable to achieve the object. The pyrolysis of step (f) above is performed in two steps including a first step and a second step, and the second step is performed at a higher temperature than that of the first step. Specifically, the first step is performed at 300 to 400° C. for 30 min to 90 min, and the second step is performed at 600 to 100° C., and preferably, at 900 to 1000° C. for 30 min to 90 min. More specifically, the first step is performed by raising the temperature to be 300° C. up to 400° C. at a rate of 1° C./min, and maintaining the temperature at 300° to 400° C. for 30 min to 90 min, and then, the second step is performed by raising the temperature to be 600° C. up to 1000° C., preferably, 900° C. up to 1000° C. at a rate of 1° C./min, and maintaining the temperature at 600° C. to 1000° C., preferably, 900° C. to 1000° C. for 30 min to 90 min. FIG. 3 illustrates non-limiting examples of pyrolysis condition in step (f), and accordingly, pyrolysis condition is not limited thereto.

In addition, the pyrolysis temperature of the second step may be selectively adjusted to control the conductivity of carbon nanowire. For example, when the pyrolysis temperature of the second step is 700° C., 800° C., and 900° C., the electrical conductivity at room temperature of the 400-nm-thick, 30-nm-wide and 10-μm-long carbon nanowire may be 800 S/m, 1,900 S/m or 14,000 S/m, respectively.

It is inferred that adopting specific pyrolysis conditions of step (f) is preferable since volume change of the micro photoresist wire is maximized and residual stress is minimized at the same time in the specific pyrolysis conditions. In particular, in specific embodiments of the pyrolysis, the volume change of the micro photoresist wire mainly occurs in the first step at which the temperature is less than 500° C. so that tensile stress developed along the wire via pyrolysis is inferred to mainly occurs in the first step at which the temperature is less than 500° C. In addition, in the specific embodiments of the pyrolysis, since the temperature may be raised to a high temperature of 600° C. to 1000° C., preferably, 900° C. to 1000° C. at a rate of 1° C./min, and maintained at 600° C. to 1000° C., preferably, 900° C. to 1000° C. for 30 min to 90 min, stress resulted from structural change is largely relieved, and accordingly, it is expected that actual stress would be small. In addition, after the pyrolysis is completed, the formed nanowire is cooled by natural cooling, and accordingly, it is expected that the residual stress is also reduced due to an annealing effect.

Specific environment in which the pyrolysis of step (f) is implemented is not specifically limited unless it disturbs the specific pyrolysis conditions. For example, the pyrolysis may be performed by putting the micro photoresist wire 14 and the photoresist post parts 13 formed in step (e) above into an electric furnace, and creating an atmosphere up to $10^{-7}$ to $10^{-5}$ torr by using a low vacuum pump and a high vacuum pump, and adopting the specific pyrolysis conditions.

After step (f) above is completed, the suspended single carbon nanowire 16 formed by the pyrolysis may be naturally cooled and taken out from the environment of pyrolysis. In addition, preferably, the carbon particles generated during the pyrolysis may be removed by using a photoresist asher.

The suspended single carbon nanowire manufactured by the manufacturing method may have a thickness of 250 nm or less and a width of 250 nm or less, preferably, a thickness of 180 nm to 240 nm and a width of 170 nm to 220 nm. In addition, the manufacturing method of the present invention is generally simple and economical as compared to the existing method for manufacturing the suspended nanowire, and accordingly, the suspended single carbon nanowire to be finally formed may have a high yield of 75% or more, preferably, 90% or more. Accordingly, the method for manufacturing the suspended single carbon nanowire has a remarkable effect of providing a suspended single carbon nanowire in a minimized dimension at a high yield.

In addition, the suspended single carbon nanowire manufactured by the manufacturing method may have a high carbon content of 95% or more, preferably, 98% or more. In general, remarkably high temperature condition of 2000° C. is theoretically required to form the carbon nanowire having a carbon content of 100% by performing pyrolysis on a polymer precursor. However, it is generally known that the pyrolysis of the polymer precursor is almost completed around 1000° C., and therefore, this limitation causes technical difficulty of the related art in that there is no choice but to use other external conditions rather than pyrolysis in order to implement a high carbon content. However, according to the manufacturing method of the present invention which adopts specific conditions as characteristic of the pyrolysis, even if the pyrolysis is completed under appropriate high temperature condition at around 1000° C., a high carbon content of the carbon nanowire may be implemented. This effect supports again that the specific condition is the condition optimized as the pyrolysis condition of the manufacturing method of the present invention.

In addition, the present invention may provide a gas sensor or an electrochemical sensor to which the suspended single carbon nanowire having improved sensitivity and reduced dimension and volume is applied by depositing a gas sensing material or an electrochemical sensing material on the suspended single carbon nanowire manufactured by the manufacturing method. The gas sensing material is not specifically limited but may be various materials known to a person skilled in the art. Preferably, the gas sensing material is a material of which conductivity is changed depending on specific gases, such as palladium or platinum. The reason is that the palladium or platinum helps improve sensitivity of the gas sensor and reduce thermal stress of the carbon nanowire. In addition, the electrochemical sensing material is not specifically limited but may be various materials known to a person skilled in the art.

In another general aspect, a method for manufacturing piled nano-electrode pairs, includes:

(a) depositing an insulation layer 51 on a substrate 50;
(b) primarily coating a photoresist 52 on the insulation layer;
(c) forming a photoresist planar electrode part 53 on an upper portion of the insulation layer by primarily exposing the primarily-coated photoresist through a photomask having a planar electrode shape;
(d) removing the photoresist of a remaining portion except for portions exposed in step (c) by performing a development process;
(e) secondarily coating the photoresist 54 on the insulation layer and the photoresist planar electrode part remaining after step (d);
(f) forming photoresist post parts 55 on an upper portion of the insulation layer by secondarily exposing the secondarily coated photoresist through a photomask having a post shape;
(g) forming a micro photoresist wire 56 connecting the photoresist post parts to each other by tertiarily exposing an upper portion of the photoresist between the photoresist post parts in a shape of a micro-sized wire connecting the photoresist post parts through a photomask having a wire shape;
(h) removing the photoresist of a remaining portion except for portions exposed in step (g) by performing a development process; and
(i) forming a planar electrode 57 and suspended carbon nanomeshes 59 by performing pyrolysis on the photoresist planar electrode parts 53, the photoresist post parts 55, and the micro-sized wire 56 remaining after step (h),
wherein the pyrolysis of step (i) is performed in two steps including a first step and a second step, the second step being performed at a temperature higher than that of the first step (FIG. 4).

A type of the substrate 50 is not specifically limited so as to achieve the object of the present invention. Preferably, the substrate may be a silicon substrate, and more preferably, a silicon wafer. Here, when the silicon wafer is used as the substrate, the substrate may have a general dimension within 6 to 9 inches.

The insulation layer 51 deposited on the substrate in step (a) above may be made of any materials capable of preventing electrical connection between two carbon posts 58 and a planar electrode 57, for example, silicon dioxide or silicon nitride. In addition, in step (a) above, the insulation layer may be preferably deposited on the entire upper surface of the substrate. Here, the deposition may be performed by non-limiting methods known to a person skilled in the art, for example, deposition by thermal oxidation.

When the substrate is an insulator in step (a) above, a step of depositing the insulation layer may be omitted. Examples of materials of the insulator substrate may include quartz, aluminum oxide, and the like.

After the insulation layer is deposited on the substrate in step (a), it is preferable to wash the deposited insulation layer through washing processes, before performing step (b) above. Here, specific methods of the washing processes are not limited, for example, washing with a piranha solution (a solution containing sulfuric acid ($H_2SO_4$) and hydrogen peroxide ($H_2O_2$) mixed at a ratio of 4:1) may be performed.

In step (b) above, the photoresist 52 may be uniformly primarily coated on the insulation layer deposited on the substrate, wherein the coating may be performed by non-limiting methods known to a person skilled in the art. For example, the coating may be performed by various methods such as spin coating, dip coating, gravure coating, and the like. The primarily coated photoresist in step (b) is not limited in principle, but preferably, may be a negative photoresist including SU-8 photoresist. Here, the primarily coated photoresist may have a thickness of 2 μm to 10 μm, preferably, 3 μm to 8 μm.

After the photoresist is primarily coated in step (b) above, it is preferable to perform a soft bake process on the insulation layer and the substrate on which the photoresist is primarily coated, before performing step (c). Here, once the soft bake is completed, step (c) which is a next step may be performed after sufficiently cooling the substrate naturally and confirming that the temperature of the substrate after being cooled is the same as that of the substrate before step (a) above. Here, specific conditions of the soft bake correspond to 80° C. to 120° C. for 1 min to 15 min.

In step (c) above, the primary exposure is performed by exposing the primarily coated photoresist to ultraviolet rays through a photomask having a planar electrode shape. When the primary exposure is completed as described above, the primarily coated photoresist is cured into a planar electrode shape on an upper portion of the insulation layer forming a photoresist planar electrode part 53. Here, the exposed light energy needs to be sufficient so that the photoresist is capable of being cured from the uppermost part of the photoresist to just above the insulation layer.

In step (d) above, the photoresist of a remaining portion except for portions exposed in step (c) may be removed by performing a development process. When the development process of step (d) is not performed, a long period of time may be required for a development process of step (h), and the planar electrode part, the photoresist post parts, and the micro-sized wire formed after step (h) may be chemically damaged to cause cracks, and therefore, the development process of step (d) needs to be essentially performed. By the development process of the photoresist of step (d), only the planar electrode part remains. In the development process, various kinds of developers known to a person skilled in the art, for example, a SU-8 developer, are usable.

In addition, according to another exemplary embodiment of the present invention, it is possible to remove the photoresist of a remaining portion except for portions exposed in steps (c) and (g) while omitting step (d) at a time by performing a development process in step (h).

In step (e), the photoresist 54 may be secondarily coated on the insulation layer and the planar electrode part remaining after step (d). Here, the coating may be performed by non-limiting various methods known to a person skilled in the art, for example, spin coating, dip coating, gravure coating, and the like. The secondarily coated photoresist in step (e) is not limited in principle, but preferably, may be a negative photoresist including SU-8 photoresist. Here, the secondarily coated photoresist has a thickness of 5 µm to 75 µm, preferably, 20 µm to 40 µm, which is thicker than that of the primarily coated photoresist in step (b).

After the photoresist is secondarily coated in step (e) above, it is preferable to perform a soft bake process on the planar electrode part, the insulation layer, and the substrate in a state in which the photoresist is secondarily coated, before performing step (f). Here, once the soft bake is completed, step (f) which is a next step may be performed after sufficiently cooling the substrate naturally and confirming that the temperature of the substrate after being cooled is the same as that of the substrate before step (a) above. Here, specific conditions of the soft bake correspond to 80° C. to 120° C. for 1 min to 15 min.

In step (f) above, the secondarily exposing may be performed beside both the sides of the planar electrode part by exposing the secondarily coated photoresist to ultraviolet rays through a photomask having a post shape. When the secondary exposure is completed as described above, the photoresist is cured into a post shape on an upper portion of the insulation layer to form the photoresist post parts 55 beside both the sides of the planar electrode part 53. Here, the exposed light energy needs to be sufficient so that the photoresist is capable of being cured from the uppermost part of the photoresist down to just above the insulation layer.

After the secondary exposure of step (f) is performed, it is preferable to perform a post exposure bake on the planar electrode part 53, the insulation layer, and the substrate in a state in which the photoresist post parts 55 are formed, before performing step (g). Here, once the post exposure bake is completed, it is required to sufficiently cool the substrate naturally and to confirm that the temperature of the substrate after being cooled is the same as that of the substrate before step (a) above. Here, specific conditions of the post exposure bake correspond to 80° C. to 120° C. for 1 min to 15 min.

In step (g), tertiary exposure is performed by exposing an upper portion of the photoresist between the photoresist post parts 55 to ultraviolet rays, through a photomask having a shape of micro-sized wire. In the tertiary exposure, only the upper end of the photoresist may be cured by limiting the energy of ultraviolet rays absorbed in the photoresist less than that of the secondary exposure. Through the tertiary exposure, a portion of the photoresist between the photoresist post parts may be cured to have a wire shape, thereby forming a micro photoresist wire 56 connecting the photoresist post parts to each other. Here, the micro photoresist wire 56 is formed so as to be separated from the insulation layer at a predetermined distance.

Meanwhile, an object of the method for manufacturing piled nano-electrode pairs according to the present invention is to form thin and dense suspended carbon nanomeshes 59, and accordingly, it is preferable to adopt an angle (θ) between the wires of the photomask having a wire shape of step (g) above to be within a range of 40 to 60 degrees, thereby achieving the object of the present invention. As illustrated in FIG. 5, it may be appreciated that when the angle (θ) between the wires of the photomask used for the tertiary exposure of step (g) above is adopted within the range of 40 to 60 degrees, the finally formed carbon nanomeshes are the most densely formed.

After the tertiary exposure of step (g) is performed, it is preferable to perform a post exposure bake on the planar electrode part 53, the insulation layer, and the substrate in a state in which the photoresist post parts 55 and the micro photoresist wire 56 are formed, before performing step (h) above. Here, once the post exposure bake is completed, it is required to sufficiently cool the substrate naturally and to confirm that a temperature of the substrate after being cooled is the same as that of the substrate before step (a) above. If the substrate is not sufficiently cooled, cracks or damage may occur on the planar electrode part 53, the photoresist post parts 55, and the micro photoresist wire 56 because of thermal stress in the development process of step (h). Here, specific conditions of the post exposure bake correspond to 80° C. to 120° C. for 1 min to 15 min.

In step (h) above, the photoresist of a remaining portion except for the exposed portions may be removed by performing a development process. The photoresist wire 56, the photoresist post parts 55, and the planar electrode part 53 in the suspended state only remain after the development process of the photoresist. In the development process, various kinds of developers known to a person skilled in the art, for example, a SU-8 developer, are usable.

After the development process of step (h) is performed, it is preferable to wash the portion remaining after the development process, before performing step (i). Specific methods for washing are not limited, for example, washing may be performed in a sequential order of isopropyl alcohol and methanol.

In addition, small residual particles, which are not removed even though the development process of step (h) is performed, may exist. Accordingly, after the development process of step (h) is performed, it is preferable to clearly remove remaining small particles which are not removed in step (h), by using a photoresist asher, before performing step (i).

In step (i), the micro photoresist wire 56, the photoresist post parts 55, and the planar electrode part 53 remaining after step (h) above may be pyrolyzed to form a planar electrode 57 and suspended carbon nanomeshes 59. The planar electrode 57 and the suspended carbon nanomeshes 59 as the piled nano-electrode pairs formed by the pyrolysis may be confirmed by FIG. 6. Here, the photoresist post parts 55 are converted into the carbon posts 58 by pyrolysis, and the planar electrode part 53 is modified into the planar electrode 57 by pyrolysis, and the carbon posts 58 allow the suspended carbon nanomeshes 59 formed by the pyrolysis to be separated from the insulation layer at a predetermined distance. In addition, in the pyrolysis, the micro photoresist wire 56 is converted into the carbon nanomeshes 59 without deflection. This is because the post parts supporting the micro photoresist wire 56 are also pyrolyzed in the pyrolysis and tensile stress is developed from the both edge of the nanomeshes formed by the pyrolysis.

Meanwhile, one of object of the method for manufacturing piled nano-electrode pairs according to the present invention is to form thin and dense suspended carbon nanomeshes, and accordingly, the present inventors found that specific conditions for the pyrolysis of step (i) is more preferable to achieve the object. The pyrolysis of step (i) above is performed in two steps including a first step and a second step, and the second step is performed at a higher temperature than that of the first step. Specifically, the first step is performed at 300 to 400° C. for 30 min to 90 min, and the second step is per formed at 600 to 1000° C. and preferably, at 900 to 1000° C. for 30 min to 90 min. More specifically, the first step is performed by raising the temperature to be 300° C. up to 4001 at a rate of 1° C./min, and maintaining the temperature at 300° C. to 400° C. for 30 min to 90 min, and then, the second step is performed by raising the temperature to be 600° C. up to 1000° C., preferably, 900° C. up to 1000° C. at a rate of 1° C./min, and maintaining the temperature at 600° C. to 1000° C., preferably, 900° C. to 1000° C. for 30 min to 90 min.

Specific environment in which the pyrolysis of step (i) is implemented is not specifically limited unless it disturbs the specific pyrolysis conditions. For example, the pyrolysis may be performed by putting the micro photoresist wire 56, the photoresist post parts 55, and the planar electrode part 53 into an electric furnace, and creating an atmosphere up to $10^{-1}$ to $10^{-5}$ torr by using a low vacuum pump and a high vacuum pump, and adopting the specific pyrolysis conditions.

After step (i) above is completed, the planar electrode 57 and the suspended carbon nanomeshes 59 formed by the pyrolysis may be naturally cooled and taken out from the environment of pyrolysis. In addition, preferably, the carbon particles generated during the pyrolysis may be removed by using a photoresist asher.

The suspended carbon nanomeshes manufactured by the manufacturing method have a width of 200 nm to 400 nm, and the carbon nanowire manufactured by the manufacturing method has an interval of 3 μm to 7 μm. In addition, since the method for manufacturing piled nano-electrode pairs is obtained by applying the method for manufacturing the suspended single carbon nanowire according to the present invention, which is simple and economical, the finally formed piled nano-electrode pairs may have a high yield of 70% or more, preferably, 80% or more. Accordingly, the method for manufacturing piled nano-electrode pairs has a remarkable effect of providing thin and dense suspended carbon nanomeshes at a high yield.

In addition, the present invention may provide a gas sensor or an electrochemical sensor to which the piled nano-electrode pairs having improved sensitivity and reduced dimension and volume are applied by depositing a gas sensing material or an electrochemical sensing material on the piled nano-electrode pairs manufactured by the manufacturing method. Here, the gas sensing material or the electrochemical sensing material may be deposited on all of the planar electrodes and the suspended carbon nanomeshes configuring the piled nano-electrode pairs, or may be deposited only on any one of the planar electrodes and the suspended carbon nanomeshes configuring the piled nano-electrode pairs. The gas sensing material is not specifically limited but may be various materials known to a person skilled in the art. Preferably, the gas sensing material is a material of which conductivity is changed depending on specific gases, such as palladium or platinum. The reason is that the palladium or platinum helps improve sensitivity of the gas sensor and reduce thermal stress of the carbon nanowire. The electrochemical sensing material is not specifically limited but may be various materials known to a person skilled in the art.

Advantageous Effects

According to the method for manufacturing the suspended single carbon nanowire of the present invention, the suspended single carbon nanowire having a minimized dimension in which a thickness is 250 nm or less and a width is 250 nm or less may be provided at a high yield, and the carbon nanowire manufactured even by pyrolysis under appropriate high temperature condition may implement high carbon content. Accordingly, it is expected that the suspended single carbon nanowire according to the present invention may effectively resolve problems of the existing suspended nanowire sensor such as reduction in yield, limitations in manufacture, and the like.

The method for manufacturing piled nano-electrode pairs according to the present invention may provide thin and dense suspended carbon nanomeshes at a high yield.

The suspended single carbon nanowire and the piled nano-electrode pairs of the present invention may have excellent electrical, mechanical, and electrochemical properties to manufacture a gas sensor or an electrochemical sensor which is improved as compared to the related art.

DESCRIPTION OF DRAWINGS

FIG. 11(b) illustrates results of concentration distribution analysis (10 mM ferrocyanide in 0.5 M KCl) of the suspended single carbon nanowire, and FIG. 11(c) illustrates results of concentration distribution analysis (10 mM ferrocyanide in 0.5 M KCl) of a planar electrode typed carbon nanowire.

[Detailed Description of Main Elements]

Figure 1:
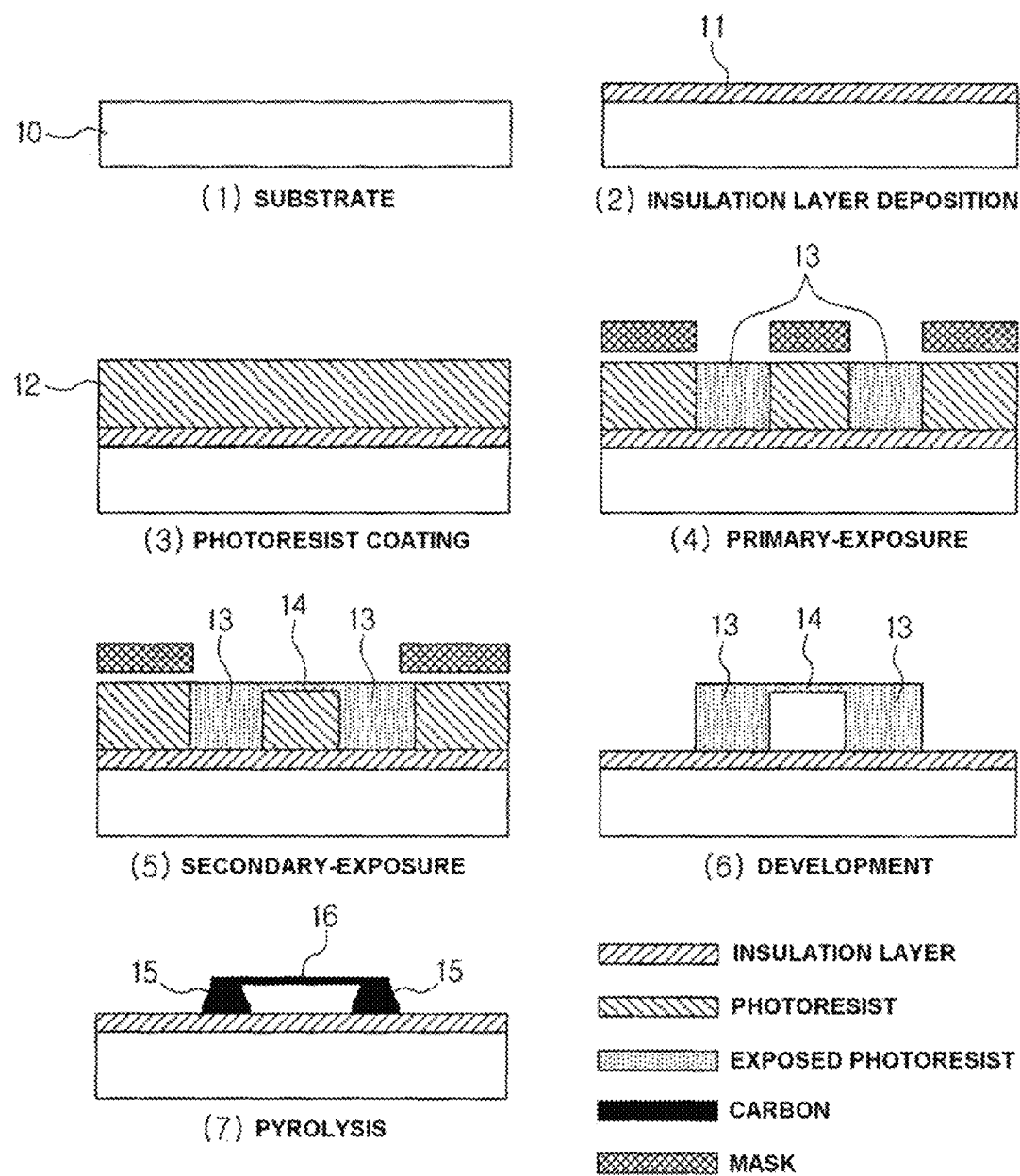
FIG. 1 is a figure illustrating a method for manufacturing a suspended single carbon nanowire.
Figure 2:
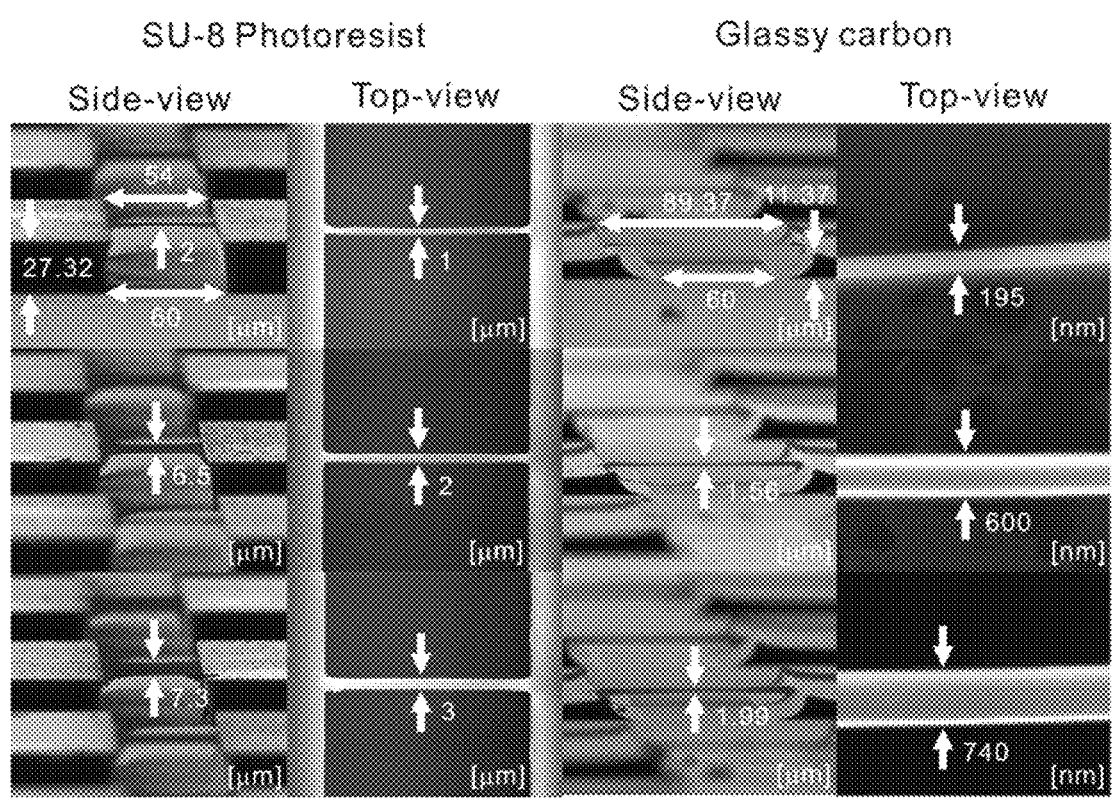
FIG. 2 is a figure comparing the structure of a micro photoresist wire before pyrolysis with that of a carbon nanowire formed after pyrolysis in the method for manufacturing a suspended single carbon nanowire.
Figure 3:
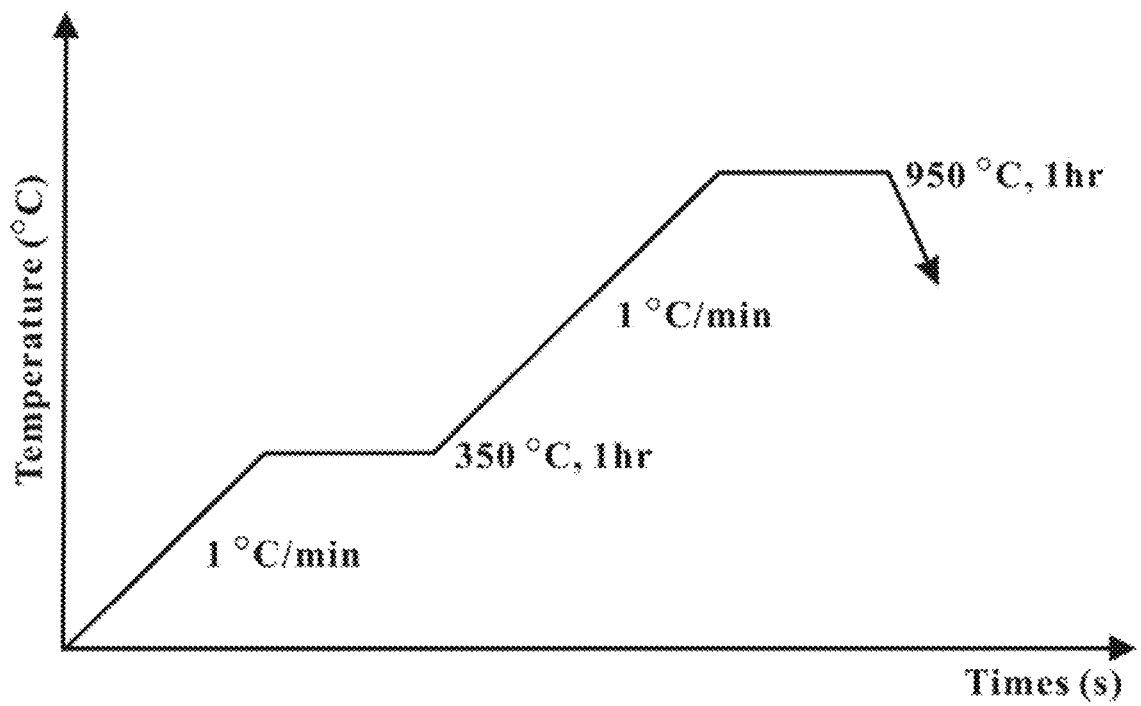
FIG. 3 illustrates an example of a pyrolysis condition in the method for manufacturing a suspended single carbon nanowire.
Figure 4:
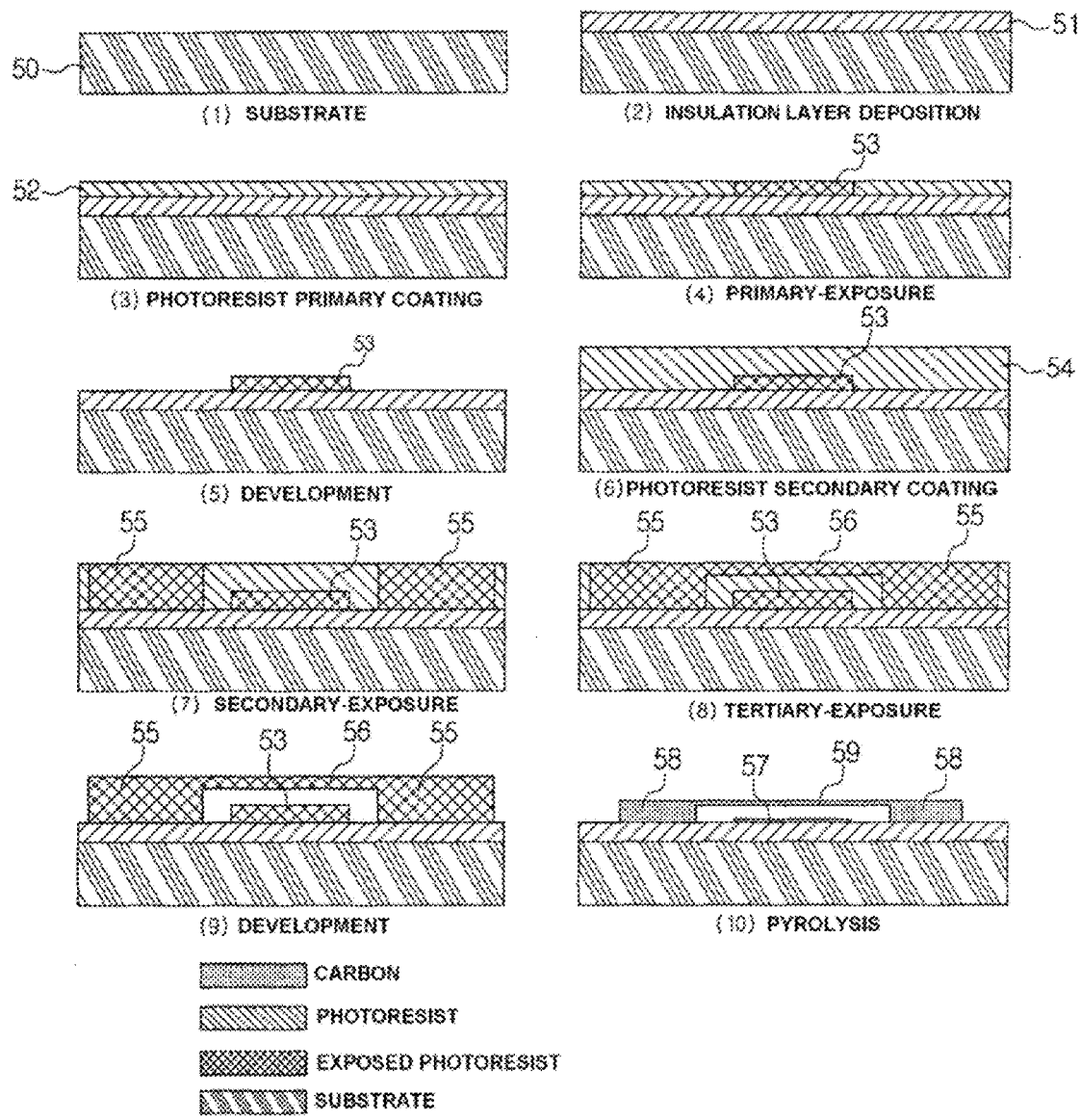
FIG. 4 is a figure illustrating a method for manufacturing piled nano-electrode pairs.
Figure 5:
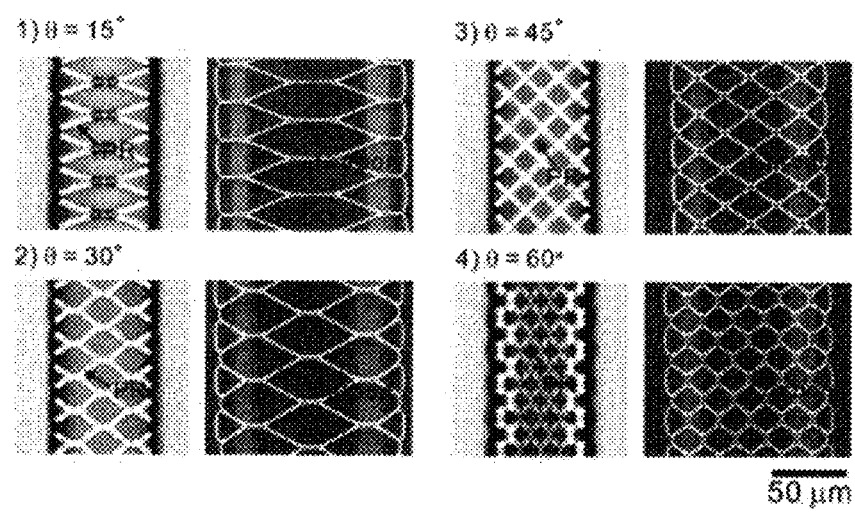
FIG. 5 illustrates density of carbon nanomeshes finally formed depending on the angle (θ) between wires of a photomask in a step of tertiarily exposing in the method for manufacturing piled nano-electrode pairs.
Figure 6:
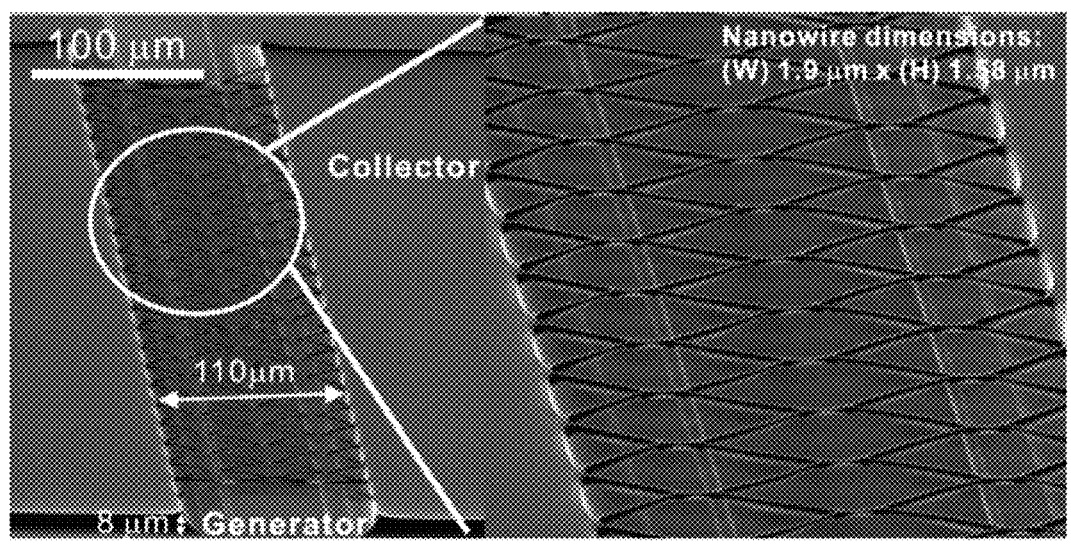
FIG. 6 illustrates piled nano-electrode pairs consisting of a planar electrode and suspended carbon nanomeshes formed by the method for manufacturing piled nano-electrode pairs.

| | |
|---|---|
| 10: Substrate | 11: Insulation layer |
| 12: Photoresist | 13: Photoresist Post Part |
| 14: Micro photoresist Wire | 15: Carbon Post |
| 16: Suspended Single Carbon nanowire | |
| 50: Substrate | 51: Insulation layer |
| 52: Primarily Coated Photoresist | |
| 53: Photoresist Planar Electrode Part | |
| 54: Secondarily Coated Photoresist | |
| 55: Photoresist Post Part | 56: Micro photoresist Wire |
| 57: Planar Electrode | 58: Carbon Post |
| 59: Suspended Carbon Nanomesh | |

BEST MODE

Hereinafter, exemplary embodiments of the present invention will be described in detail. The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe most appropriately the best method he or she knows for carrying out the invention.

Therefore, the configurations described in the embodiments and drawings of the present invention are merely most preferable embodiments but do not represent all of the technical spirit of the present invention. Thus, the present invention should be construed as including all the changes, equivalents, and substitutions included in the spirit and scope of the present invention at the time of filing this application.

Example 1

Manufacture of Suspended Single Carbon Nanowire

Silicon dioxide as an insulation layer was deposited on a general 6 inch silicon wafer by thermal oxidation, and a washing process (using a Piranha solution containing sulfuric acid ($H_2SO_4$) and hydrogen peroxide ($H_2O_2$) mixed at a ratio of 4:1) was performed. SU-8 which is a photoresist was uniformly coated on the insulation layer at a thickness of 25 μm by spin coating, and then soft bake was performed at 95° C. for 9 min. After the soft bake was performed, the silicon wafer was sufficiently cooled naturally to confirm that a temperature of the silicon wafer after being cooled is the same as that of the silicon wafer at an initial state. After the silicon wafer was sufficiently cooled, the primary exposure was performed by sufficiently exposing the photoresist to ultraviolet rays through a photomask having a post shape by using a mask aligner, and post exposure bake was performed at 95° C. for about 3 min, and the silicon wafer was sufficiently cooled again. After the silicon wafer was sufficiently cooled, the secondary exposure was performed by sufficiently exposing the photoresist to ultraviolet rays through a photomask having a wire shape. After the secondary exposure was performed, post exposure bake was performed at 95° C. for about 3 min, and the silicon wafer was sufficiently cooled again. After the silicon wafer was sufficiently cooled again, the photoresist of a remaining portion except for the exposed portions was removed by a development process with an SU-8 developer. After the development process, washing was performed in a sequential order of isopropyl alcohol and methanol, and any remaining small particles which were not removed were clearly removed, by using a photoresist asher, in consideration that small particles which are not removed during the development process remain. The micro SU-8 wire and the SU-8 post parts in a clean state were put into an electric furnace, and an atmosphere was created up to $10^{-6}$ torr by using a low vacuum pump and a high vacuum pump, and then pyrolysis was performed in two steps including a first step and a second step. Specifically, the first step was performed by raising a temperature up to 350° C. at a rate of 1° C./min, and maintaining the temperature at 350° C. for 60 min, and then, the second step was performed by raising a temperature up to 900° C. at a rate of it/min, and maintaining the temperature at 900° C. for 60 min. The suspended single carbon nanowire formed after the pyrolysis was naturally cooled and taken out from the electric furnace, and carbon particles generated during the pyrolysis were removed by using a photoresist asher.

Example 2

Analysis of Physical Properties of Suspended Single Carbon Nanowire of Example 1

Figure 7:
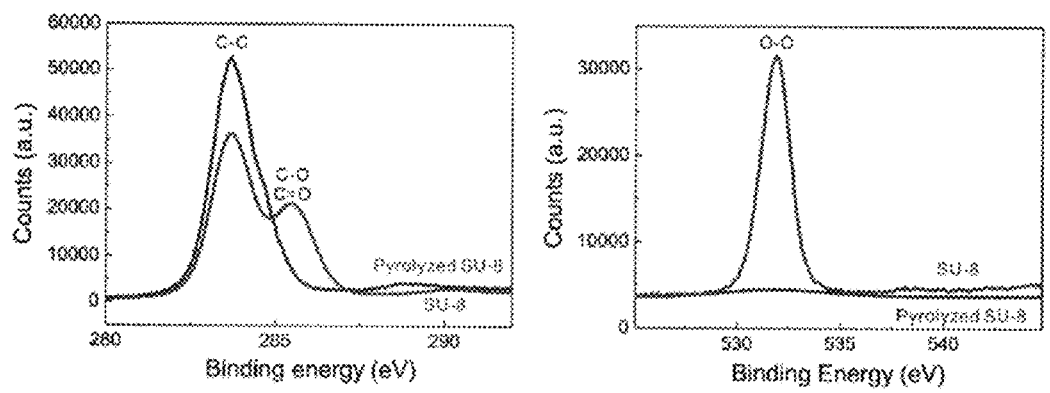
FIG. 7 illustrates analysis result of binding and composition of carbon (left), oxygen (right), and other elements at the suspended carbon nanomeshes using X-ray Photoelectron Spectroscopy (XPS).

The suspended single carbon nanowire finally manufactured by Example 1 had a yield of 90%. The shape and structural characteristics of the suspended single carbon nanowire were measured by using SEM (Quanta 200, FEI Company, USA), HRTEM (JEM-2100F, JEOL Ltd., Japan), FIB (Quanta 3D FEG, FET Company, USA), and Raman spectroscopic system (alpha300R, WITec GmbH, Germany). It was measured that the suspended single carbon nanowire had a thickness of 210 nm and a width of 195 nm. In addition, in order to measure the carbon content of the manufactured suspended single carbon nanowire, X-ray photoelectron spectroscopy was used, wherein it is not easy to directly measure the suspended single carbon nanowire since a beam of the X-ray photoelectron spectroscopy has a several micron size, and therefore, a carbon post portion supporting the wire was analyzed. As analysis results, many changes in contents of C—C, C—C, and O—O before and after performing the pyrolysis were observed, and the carbon content after the pyrolysis was measured as 96.9%. Specifically, as illustrated in FIG. 7, it was confirmed that after the pyrolysis, a content of C—C was increased, and contents of C—O and O—O rarely exist.

Comparative Example 1

Comparative Example 1 was performed by the same method as Example 1 except for applying a single step under pyrolysis condition at 300° C. for 2 min.

Comparative Example 2

Comparative Example 2 was performed by the same method as Example 1 except for applying a single step under pyrolysis condition at 350° C. for 2 min.

Comparative Example 3

Comparative Example 3 was performed by the same method as Example 1 except for applying a single step under pyrolysis condition at 400° C. for 2 min.

Comparative Example 4

Comparative Example 4 was performed by the same method as Example 1 except for applying a single step under pyrolysis condition at 450° C. for 2 min.

Comparative Example 51

Comparative Example 5 was performed by the same method as Example 1 except for applying a single step under pyrolysis condition at 500° C. for 2 min.

Comparative Example 6

Comparative Example 6 was performed by the same method as Example 1 except for applying a single step under pyrolysis condition at 500° C. for 60 min.

Comparison Among Example 1 and Comparative Examples

TABLE 1

| Pyrolysis Condition [° C.]-[min] | Suspended Single Carbon Nanowire | | Carbon Post |
|---|---|---|---|
| | Width (nm) | Length (μm) | Height (μm) |
| 300° C. for 2 min (Comparative Example 1) | 675 | 63.53 | 20.16 |
| 350° C. for 2 min (Comparative Example 2) | 495 | 79.15 | 15.3 |
| 400° C. for 2 min (Comparative Example 3) | 430 | 82.70 | 12.91 |
| 450° C. for 2 min (Comparative Example 4) | 359 | 84.41 | 11.52 |
| 500° C. for 2 min (Comparative Example 5) | 305 | 85.02 | 11.36 |
| 500° C. for 60 min (Comparative Example 6) | 296 | 85.75 | 10.62 |
| 350° C. for 60 min and 900° C. for 60 min (Example 1) | 195 | 89.37 | 9.97 |

As described in [Table 1], it may be appreciated that according to the manufacturing method of the present invention in which the specific condition is adopted as a pyrolysis condition, the suspended single carbon nanowire in a minimized dimension having a width of 250 nm or less may be provided. This result supports that the specific condition is the condition optimized as the pyrolysis condition of the manufacturing method of the present invention.

Example 3

Manufacture of Piled Nano-Electrode Pairs

Silicon dioxide as an insulation layer was deposited on a general 6 inch silicon wafer by thermal oxidation, and then SU-8 which is a photoresist was uniformly coated on the insulation layer at a thickness of 7 μm by spin coating. After primarily coating the SU-8 photoresist, primary exposure was performed by sufficiently exposing the photoresist to ultraviolet rays through a photomask having a planar electrode shape, and a remaining portion except for the primarily exposed portions was removed by performing a development process using an SU-8 developer. After performing the development process, the SU-8 photoresist was uniformly coated on the insulation layer and the planar electrode part at a thickness of 25 μm by spin coating. After secondarily coating the SU-8 photoresist, secondary exposure was performed by sufficiently exposing the photoresist to ultraviolet rays through a photomask having a post shape, and tertiary exposure was performed by sufficiently exposing the photoresist to ultraviolet rays through a photomask in which an angle θ between wires of the photomask is 45 degrees. After the tertiary exposure, the photoresist of a remaining portion except for the exposed portions was removed by development using an SU-8 developer. After performing the development, the micro SU-8 wire, the SU-8 post parts, and the SU-8 planar electrode part were put into an electric furnace, and an atmosphere was created up to $10^{-6}$ torr by using a low vacuum pump and a high vacuum pump, and then pyrolysis was performed in two steps including a first step and a second step. Specifically, the first step was performed by raising a temperature up to 350° C. at a rate of 1° C./min, and maintaining the temperature at 350° C. for 60 min, and then, the second step was performed by raising a temperature up to 900° C. at a rate of 1° C./min, and maintaining the temperature at 900° C. for 60 min. The planar electrode and the suspended carbon nanomeshes formed after the pyrolysis were naturally cooled and taken out from the electric furnace.

Example 4

Analysis of Physical Properties of Piled Nano-Electrode Pairs of Example 3

Figure 8:
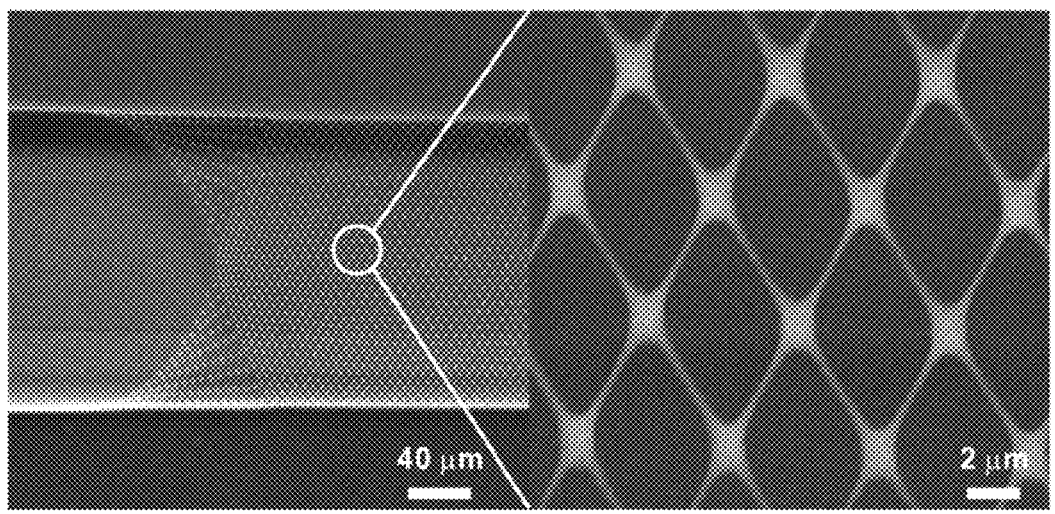
FIG. 8 illustrates shapes of suspended carbon nanomeshes having a dense form which are finally formed by Example 3.

The piled nano-electrode pairs finally manufactured by Example 3 had a yield of 75%. The shape and structural characteristics of the suspended carbon nanomeshes were measured by using SEM (Quanta 200, FEI Company, USA), HRTEM (JEM-2100F, JEOL Ltd., Japan), FIB (Quanta 3D FEG, FET Company, USA), and Raman spectroscopic system (alpha300R, WITec GmbH, Germany). It was measured that the suspended carbon nanomeshes had a width of 300 nm, and the carbon nanowire had a gap of 4.5 μm (FIG. 8).

Example 5

Observation of Electrical Properties of Suspended Single Carbon Nanowire of Example 1

Figure 9:
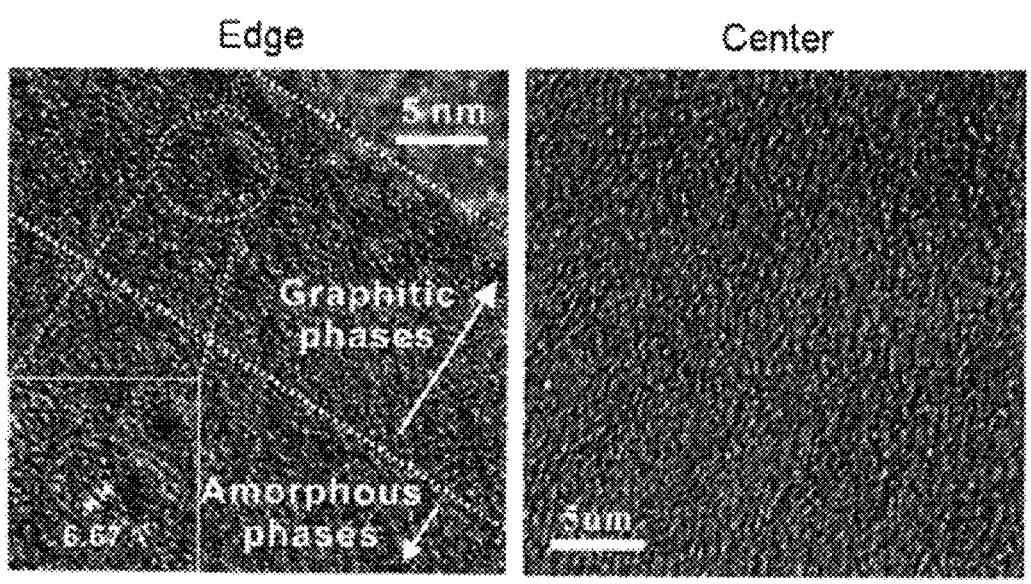
FIG. 9 illustrates degree of crystallization of the suspended single carbon nanowire measured using transmission electron microscopy.

FIG. 9 illustrates crystallinity of the suspended single carbon nanowire measured by using transmission electron microscopy. It is known that energy band gap reduces as the ratio of graphitic phase increases, and it was found in the transmission electron microscopy image that crystallinity of the graphitic phase at edges was higher than that of the center of the carbon nanowire. Even though the temperature condition of the pyrolysis was lower than a temperature at which the graphitic phase is formed, the volume ratio of graphitic phases was approximately 20%; this means that the carbon wire has high electrical conductivity even though the suspended single carbon nanowire is glassy carbon.

Example 6

Observation of Mechanical Properties of Suspended Single Carbon Nanowire of Example 1

Figure 10:
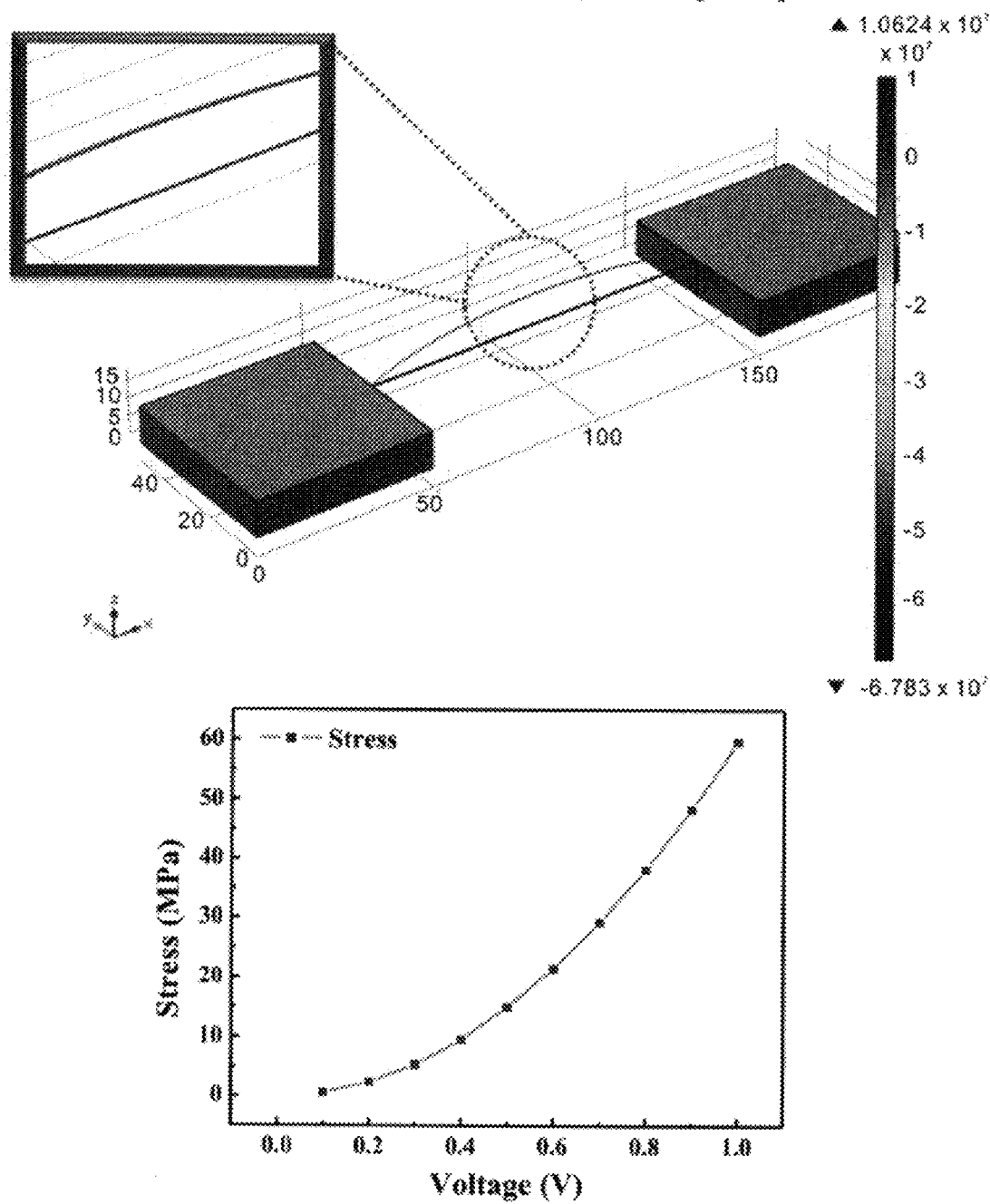
FIG. 10 illustrates analysis results of stress generated at a suspended single carbon nanowire caused by applying voltage.

FIG. 10 illustrates stress generated at the suspended single carbon nanowire by applying voltage. Data of the volume expansion rate of common carbon is used for the volume expansion rate of the carbon nanowire depending on temperatures. Stress was also the maximum in the center of the nanowire, and results obtained by analyzing the maximum stress depending on applied voltages are illustrated in a graph of FIG. 10. Volume expansion depending on temperature increase generates compressive stress to the suspended single carbon nanowire; however, the maximum compressive stress of up to IV does not reach actual breaking stress of carbon. This means that the suspended single carbon nanowire manufactured by Example 1 had excellent mechanical properties.

Example 7

Observation of Electrochemical Properties of Suspended Single Carbon Nanowire of Example 1

Figure 11:
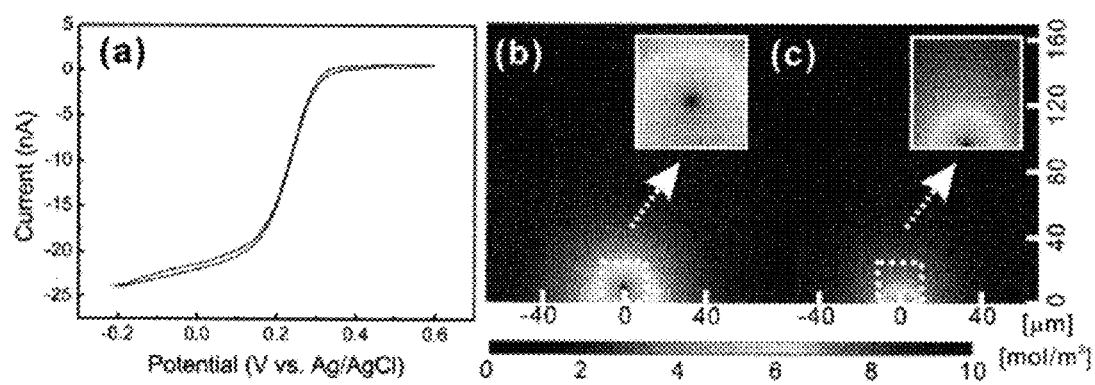
FIG. 11 illustrates electrochemical properties of the suspended single carbon nanowire and characteristics thereof as a suspended electrochemical sensor using cyclic voltammetry experiment. Specifically, FIG. 11(*a*) illustrates analysis results of electrochemical properties of the suspended single carbon nanowire through cyclic voltammetry experiment.

Electrochemical properties of the suspended single carbon nanowire and characteristics thereof as a suspended electrochemical sensor through cyclic voltammetry experiment are shown in FIG. 11. For the characterization of the electrochemical properties of the suspended single carbon nanowire, cyclic voltammetry experiment was performed and it showed that the suspended single carbon nanowire had high diffusion-limited current. Simulation of the concentration distribution caused by redox reactions were simulated using Comsol Multiphysics software in order to find structural difference between the suspended electrode and the planar electrode. Its results confirmed that the suspended nanowire generated diffusion-limited current per unit length two times more than a planar nanowire of which area is the same cross-sectional area as that of the suspended nanowire. In addition, it was found that current signal from the nanowire positioned to be spaced apart from the substrate at a predetermined distance or more (>8 μm) was almost the same as that of a nanowire positioned to be spaced apart from the substrate at several tens of micrometers (μm) or more. Therefore, according to the present invention, advantages of the suspended single carbon nanowire may be sufficiently utilized without positioning the nanowire to be spaced apart from the substrate at several tens of micrometers or more. It means that the suspended single carbon nanowire manufactured by Example 1 has excellent electrochemical properties.

The invention claimed is:

1. A method for manufacturing a suspended single carbon nanowire comprising:
    (a) depositing an insulation layer on a substrate;
    (b) coating a photoresist on the insulation layer;
    (c) forming photoresist post parts on an upper portion of the insulation layer by primarily exposing the photoresist through a photomask having a post shape;
    (d) forming a micro photoresist wire connecting the photoresist post parts to each other by secondarily exposing an upper portion of the photoresist between the photoresist post parts in a shape of a micro-sized wire connecting the photoresist post parts through a photomask having a wire shape;
    (e) removing the photoresist of a remaining portion except for portions exposed in steps (c) and (d) by performing a development process; and
    (f) creating a vacuum condition, and forming the suspended single carbon nanowire by pyrolyzing the photoresist post parts and the micro-sized wire remaining after step (e),
    wherein the pyrolysis of step (f) is performed in two steps including a first step and a second step, the second step being performed at a temperature higher than that of the first step.

2. The method of claim 1, wherein the substrate is a silicon substrate.

3. The method of claim 1, wherein the insulation layer is made of silicon dioxide or silicon nitride.

4. The method of claim 1, wherein the photoresist is SU-8 photoresist.

5. The method of claim 1, wherein in the pyrolysis of step (f), the first step is performed at 300° C. to 400° C. for 30 min to 90 min, and the second step is performed at 900° C. to 1000° C. for 30 min to 90 min.

6. The method of claim 5, wherein the suspended carbon nanowire has a thickness of 250 nm or less and a width of 250 nm or less.

7. The method of claim 6, wherein the thickness is 180 nm to 240 nm and the width is 170 nm to 220 nm.

8. A method for manufacturing piled nano-electrode pairs, comprising:
    (a) depositing an insulation layer on a substrate;
    (b) primarily coating a photoresist on the insulation layer;
    (c) forming a photoresist planar electrode part on an upper portion of the insulation layer by primarily exposing the primarily-coated photoresist through a photomask having a planar electrode shape;
    (d) removing the photoresist of a remaining portion except for portions exposed in step (c) by performing a development process;
    (e) secondarily coating a photoresist on the insulation layer and the photoresist planar electrode part remaining after step (d);
    (f) forming photoresist post parts on an upper portion of the insulation layer by secondarily exposing the secondarily coated photoresist through a photomask having a post shape;
    (g) forming a micro photoresist wire connecting the photoresist post parts to each other by tertiarily exposing an upper portion of the photoresist between the photoresist post parts in a shape of a micro-sized wire connecting the photoresist post parts through a photomask having a wire shape;
    (h) removing the photoresist of a remaining portion except for portions exposed in step (g) by performing a development process; and
    (i) creating a vacuum condition, and forming a planar electrode and suspended carbon nanomeshes by performing pyrolysis on the photoresist planar electrode parts, the photoresist post parts, and the micro-sized wire remaining after step (h),
    wherein the pyrolysis of step (i) is performed in two steps including a first step and a second step, the second step being performed at a temperature higher than that of the first step.

9. The method of claim 8, wherein the substrate is a silicon substrate.

10. The method of claim 8, wherein the insulation layer is made of silicon dioxide or silicon nitride.

11. The method of claim 8, wherein the primarily coated photoresist and the secondarily coated photoresist are SU-8 photoresist.

12. The method of claim 8, wherein the secondarily coated photoresist is thicker than the primarily coated photoresist.

13. The method of claim 8, wherein an angle (θ) between wires of the photomask having a wire shape is 40 to 60 degrees.

14. The method of claim 8, wherein the first step is performed at 300° C. to 400° C. for 30 min to 90 min, and the second step is performed at 900° C. to 1000° C. for 30 min to 90 min.

15. The method of claim 14, wherein the suspended carbon nanomeshes have a width of 200 nm to 400 nm, and a carbon nanowire has a gap of 3 μm to 7 μm.

* * * * *